United States Patent
Puckett

(10) Patent No.: US 9,901,471 B2
(45) Date of Patent: Feb. 27, 2018

(54) SPRING ASSISTED MEDICAL DEVICE DEPLOYMENT ASSEMBLY

(71) Applicant: Cook Medical Technologies LLC, Bloomington, IN (US)

(72) Inventor: Dean Puckett, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 229 days.

(21) Appl. No.: 14/149,071

(22) Filed: Jan. 7, 2014

(65) Prior Publication Data

US 2014/0214046 A1 Jul. 31, 2014

Related U.S. Application Data

(60) Provisional application No. 61/758,336, filed on Jan. 30, 2013.

(51) Int. Cl.
*A61F 2/06* (2013.01)
*A61F 2/966* (2013.01)

(52) U.S. Cl.
CPC ......... *A61F 2/966* (2013.01); *A61M 2205/10* (2013.01)

(58) Field of Classification Search
CPC ...... A61F 2/966; A61F 2/95; A61F 2002/011; A61F 2002/9505; A61F 2/01; A61F 2/2427; A61F 2/2436; A61F 11/002; A61F 2/2466; A61B 2017/1205; A61B 17/3468; A61B 17/10; A61B 17/12; A61B 2017/00623
USPC .... 623/1.11, 1.12, 1.23, 2.11; 606/108, 200, 606/213, 181, 182
See application file for complete search history.

(56) References Cited

U.S. PATENT DOCUMENTS

| 6,149,664 | A | * | 11/2000 | Kurz | A61B 17/12022 |
| | | | | | 606/108 |
| 7,163,552 | B2 | * | 1/2007 | Diaz | A61F 2/95 |
| | | | | | 623/1.12 |
| 7,867,267 | B2 | | 1/2011 | Sullivan et al. | |
| 7,993,384 | B2 | | 8/2011 | Wu et al. | |
| 2005/0240254 | A1 | * | 10/2005 | Austin | A61F 2/95 |
| | | | | | 623/1.11 |
| 2007/0106324 | A1 | * | 5/2007 | Garner | A61F 2/013 |
| | | | | | 606/200 |
| 2007/0260301 | A1 | * | 11/2007 | Chuter | A61F 2/95 |
| | | | | | 623/1.11 |
| 2007/0299461 | A1 | * | 12/2007 | Elliott | A61B 17/12022 |
| | | | | | 606/191 |
| 2009/0192518 | A1 | * | 7/2009 | Golden | A61F 2/95 |
| | | | | | 606/108 |
| 2011/0144735 | A1 | * | 6/2011 | Hartley | A61F 2/95 |
| | | | | | 623/1.11 |

(Continued)

*Primary Examiner* — Corrine McDermott
*Assistant Examiner* — Majid Jamialahmadi
(74) *Attorney, Agent, or Firm* — Liell & McNeil

(57) ABSTRACT

A medical device deployment assembly includes a retractable sheath and a catheter positioned inside the retractable sheath. A medical device is compressed between an outer surface of the catheter and an inner surface of the retractable sheath. A spring is positioned inside the retractable sheath, and a pusher band is positioned inside the retractable sheath between the medical device and the spring. The spring biases the medical device deployment assembly toward a deployment configuration in which a distal tip of the retractable sheath is proximal to a proximal tip of the medical device.

20 Claims, 3 Drawing Sheets

(56) References Cited

U.S. PATENT DOCUMENTS

2013/0281787 A1* 10/2013 Avneri .............. A61M 25/0133
                                                                600/208
2013/0304179 A1* 11/2013 Bialas .................... A61F 2/966
                                                                623/1.11

\* cited by examiner

SPRING ASSISTED MEDICAL DEVICE DEPLOYMENT ASSEMBLY

TECHNICAL FIELD

The present disclosure relates generally to a spring assisted medical device deployment assembly, and more particularly to a spring configured to bias the medical device deployment assembly toward a deployment configuration.

BACKGROUND

Various medical devices, including stents, stent grafts, and venous filters, are deployed within the vasculature of a patient using deployment devices. Some of the medical devices are self-expanding, in a radial direction, and require restriction from radial expansion prior to deployment. According to some deployment systems, an outer sheath maintains a restricted position of the self-expanding medical device during advancement of the medical device to a deployment site. Once the medical device is positioned at or near the deployment site, the sheath is removed, or retracted, to permit radial expansion of the self-expanding medical device. The retraction of the sheath is typically facilitated through manipulation of a handle positioned at a proximal end of the deployment system.

Although a variety of different deployment systems exist, ranging from relatively simple to relatively complex devices, a conventional system with a pull-type handle includes a proximal handle portion and a distal handle portion. The proximal handle portion is configured to maintain a relatively stationary position of a pusher catheter, which supports the self-expanding medical device, while the distal handle portion is configured to retract a sheath positioned over the self-expanding medical device. Deployment of the medical device is initiated by proximally retracting the distal handle portion, which is connected to the sheath, toward the proximal handle portion, which is connected to the pusher catheter. This conventional deployment system, in particular, may be incapable of providing the deployment forces required for deploying relatively large medical devices, which may include specialized coatings.

U.S. Patent Application Publication No. 2007/0219617 to Saint discloses a handle for a long self expanding stent. In particular, the handle includes a housing and a spool. A pushrod has a proximal end connected to the housing of the handle. A retraction wire is connected to a proximal end of a sheath and to the spool. Refraction of the sheath is accomplished by winding the retraction wire around the spool. Accordingly, the handle may be shorter than the stent. Although the handle of the Saint disclosure may be useful for some applications, it should be appreciated that there is a continuing need for efficient and effective handles for medical device deployment systems.

The present disclosure is directed toward one or more of the problems or issues set forth above.

SUMMARY OF THE DISCLOSURE

In one aspect, a medical device deployment assembly includes a retractable sheath and a catheter positioned inside the retractable sheath. A medical device is compressed between an outer surface of the catheter and an inner surface of the retractable sheath. A spring is positioned inside the retractable sheath, and a pusher band is positioned inside the retractable sheath between the medical device and the spring. The spring biases the medical device deployment assembly toward a deployment configuration in which a distal tip of the retractable sheath is proximal to a proximal tip of the medical device.

In another aspect, a method of deploying a medical device within a body lumen using the medical device deployment assembly described above is also provided. The method includes steps of positioning the medical device of the medical device deployment assembly at a deployment location, and deploying the medical device at the deployment location. The deploying step includes sliding the retractable sheath with respect to the catheter while maintaining the catheter stationary with respect to the deployment location. The sliding step includes pushing the retractable sheath with respect to the catheter with a pushing force using the spring.

DETAILED DESCRIPTION

Figure 1:
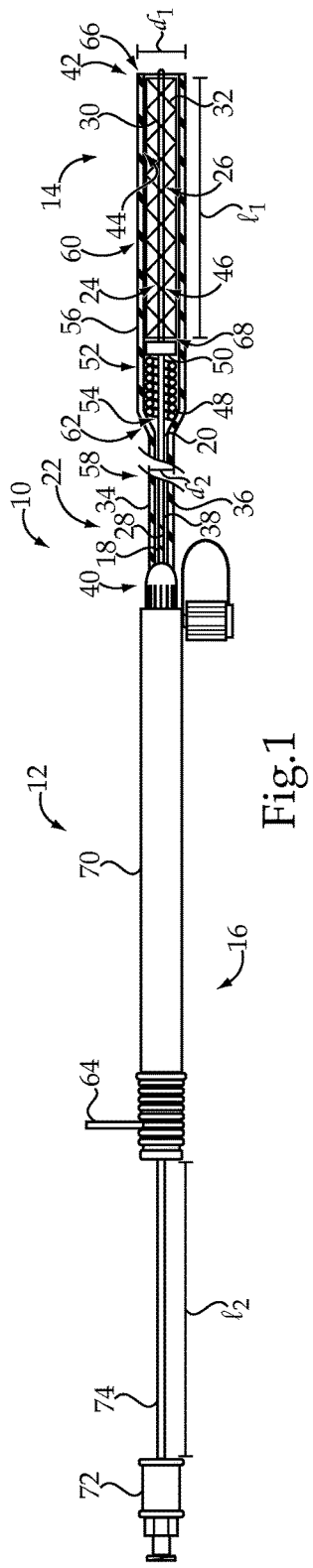
FIG. 1 is a partially sectioned side diagrammatic view of a medical device deployment assembly, according to one embodiment of the present disclosure, shown in a pre-deployment configuration.

Referring to FIG. 1, there is shown a medical device deployment assembly 10 according to one embodiment of the present disclosure. The medical device deployment assembly 10 may include a number of components, which may be provided within a sterile, tear open package (not shown), as is known in the art. In performing a medical device deployment procedure on a patient, the components of the medical device deployment assembly 10 and additional components may be used, depending upon the specifics of the procedure to be performed. As should be appreciated, however, components of the medical device deployment assembly 10 might be separately packaged and/or the medical device deployment assembly 10 might also include components in addition to those shown, including components routinely used in percutaneous vascular procedures.

In general, the medical device deployment assembly 10 has a proximal end 12 and a distal end 14. As shown, a handle assembly 16, which may include relatively rigid components made from medical grade materials, is disposed at the proximal end 12. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

According to the exemplary embodiment, the medical device deployment assembly 10 includes an inner shaft, or catheter, 18 having an elongate body 20, a proximal end 22, a distal end 24, and a medical device support region 26 at the distal end 24 of the elongate body 20. According to some embodiments, the inner shaft 18, which may include a hollow tubular body defining a lumen 28, may range in length from several inches to several feet long, and may have a catheter wall diameter that is orders of magnitude smaller than its length. The elongate body 20 may be made from any common medical tube material, such as, for example, a plastic, rubber, silicone, or Teflon material, and may exhibit both firmness and flexibility.

A medical device 30 may be positioned over the inner shaft 18 at the medical device support region 26. According to the exemplary embodiment, the medical device 30 may include a radially expanding stent 32 for providing tubular support within a blood vessel, canal, duct, or other bodily passageway. Radially expandable stents 32 are known and may be expanded using a balloon, or other known device, positioned at a distal portion of a delivery catheter, such as catheter 18. Alternatively, and according to the exemplary embodiment, the radially expanding stent 32 may be made from a resilient or shape memory material, such as, for example, nitinol, that is capable of self-expanding from a compressed state to an expanded state without the application of a radial force on the stent 32. Such a stent 32 may be referred to as a "self-expanding" stent 32. Although a self-expanding stent 32 will be discussed herein, those skilled in the art should appreciate that the medical device 30 may include alternative radially expandable prosthetic implants. For example, the medical device 30 may include a self-expanding, or otherwise expandable, stent graft or venous filter.

According to some embodiments, an axial length of the self-expanding stent 32 may be greater than about 100 mm. According to some embodiments, the medical device may have an axial length of between about 10 mm and 300 mm. More particularly, the medical device may range from 20 mm in length to 200 mm in length. It should be appreciated that such dimensions are provided for exemplary purposes only, and a variety of medical devices, having various sizes and configurations, may be deployed using the medical device deployment assembly 10 described herein. Further, the self-expanding stent 32 may include a specialized coating, as is known to those skilled in the art.

A retractable sheath 34 has an elongate tubular body 36 defining a lumen 38 extending from an open proximal end 40 to an open distal end 42. As shown, the catheter 18 is telescopically received within the retractable sheath 34. When the self-expanding stent 32, or other medical device, is loaded onto the catheter 18, the self-expanding stent 32 may be restricted from self-expansion using the elongate tubular sheath 34, which is slidably received over the elongate tubular body 20 of the catheter 18. According to this configuration, the retractable sheath 34 restricts radial expansion of the self-expanding stent 32 by contacting the stent 32 with an inner wall surface 44 defining the lumen 38 of the retractable sheath 34. In particular, the medical device 30 is compressed between an outer surface 46 of the catheter 18 and the inner surface 44 of the retractable sheath 34. According to some embodiments, a ratio of a length $l_1$ of the medical device 30 to an outer diameter $d_1$ of the retractable sheath 34 is greater than fifty.

A spring 48, such as a compression spring or other similar spring member, is positioned inside the retractable sheath 34 and over the catheter 18. A pusher band 50 is also positioned inside the retractable sheath 34, and is located between the medical device 30 and the spring 48. In particular, the pusher band 50 may be disposed on the exterior 46 of the catheter 18 proximal to the medical device 30 and may be configured to restrict proximal movement of the medical device 30 during relative movement of the catheter 18 and the retractable sheath 34. According to some configurations, a distal end 52 of the spring 48 is configured to contact the pusher band 50, while a proximal end 54 of the spring 48 is configured to contact an inner portion of the retractable sheath 34.

According to the exemplary embodiment, the retractable sheath 34 may be a stepped sheath 56 with a long proximal segment 58 having a small diameter $d_2$ and a short distal segment 60 having a large diameter $d_1$. The spring 48 may be compressed between the pusher band 50 and a transition shoulder 62 of the stepped sheath 56 where the sheath 56 transitions from the long proximal segment 58 to the short distal segment 60. For example, as the medical device 30 is loaded onto the catheter 18 and into the retractable sheath 34, the spring 48 may be compressed between the transition shoulder 62 and the pusher band 50. According to some embodiments, the spring 48 may be compressed with a pre-load of at least five Newtons. A locking pin 64, which is known to those skilled in the art, may be provided, in the pre-deployment configuration of FIG. 1, to fix the relative positions of the catheter 18 and the retractable sheath 34. With the locking pin 64 removed, the spring 48 may be permitted to bias the medical device deployment assembly 10 toward a deployment configuration, as shown in FIG. 2, in which a distal tip 66 of the retractable sheath 34 is proximal to a proximal tip 68 of the medical device 30.

Figure 2:
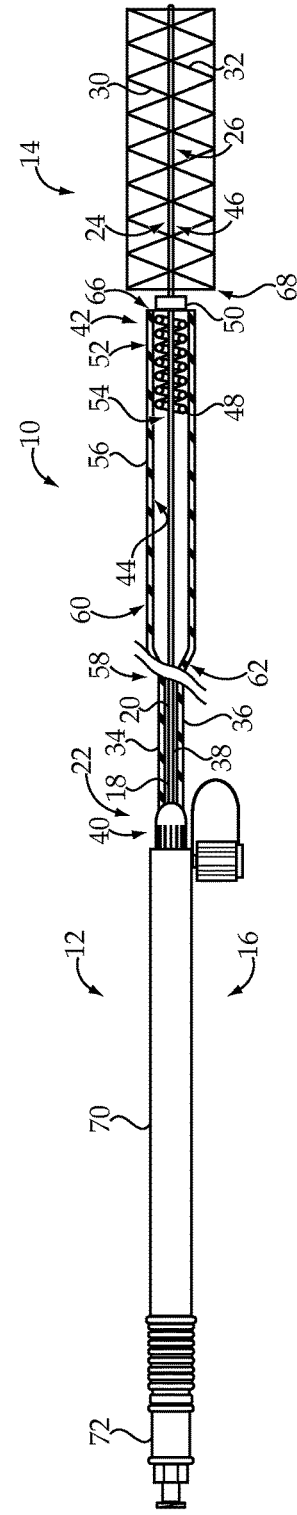
FIG. 2 is a partially sectioned side diagrammatic view of the medical device deployment assembly of FIG. 1, shown in a deployment configuration.

To facilitate movement of the medical device deployment assembly 10 between the pre-deployment configuration of FIG. 1 and the deployment configuration of FIG. 2, a clinician may manipulate the handle assembly 16. According to one example, the handle assembly 16 may include a handle 70 attached to the proximal end 40 of the retractable sheath 34, and a hub 72 and cannula 74 operatively coupled to the proximal end 22 of the catheter 18. The hub 72 is located a deployment distance $l_2$ proximal of the handle 70 in the pre-deployment configuration of FIG. 1, with the deployment distance $l_2$ being greater than a length $l_1$ of the medical device 30. To move the medical device deployment assembly 10 into the deployment configuration of FIG. 2, and with the locking pin 64 removed, the clinician may maintain a stationary position of the hub 72, while proximally retracting the handle 70 along the cannula 74. The handle 70 is moved toward, and eventually contacts, the hub 72 in the deployment configuration, as shown in FIG. 2.

The spring 48 may provide an additional force as the medical device deployment assembly 10 begins the transition from the pre-deployment configuration to the deployment configuration. In particular, the distal end 52 of the spring 48 may provide a distal force against the pusher band 50, which may have a fixed position relative to the catheter 18, while the proximal end 54 of the spring 48 may provide a proximal force against the transition shoulder 62 of the retractable sheath 34. This additional force may be particularly useful when deploying a relatively large medical device and/or when deploying a medical device having a specialized coating, which may introduce additional friction between the coated medical device and other components of the deployment system. For example, the medical device 30 may be coated with Paclitaxel, which helps prevent an artery from narrowing again.

Figure 3:
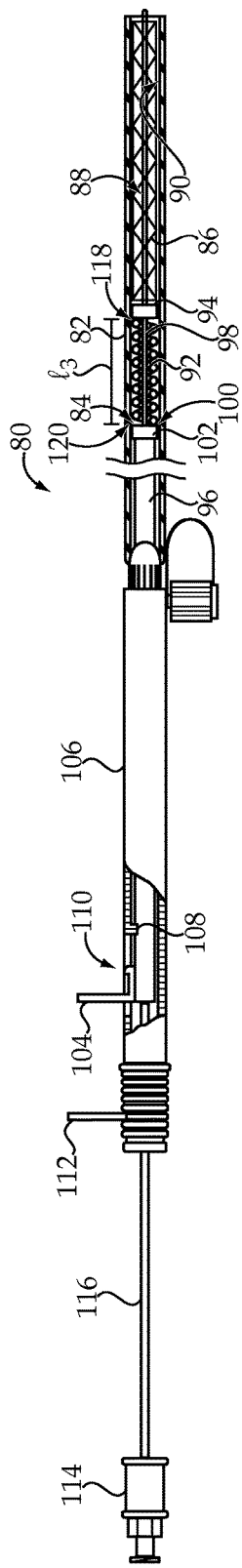
FIG. 3 is a partially sectioned side diagrammatic view of a medical device deployment assembly, according to another embodiment of the present disclosure, shown in a relaxed configuration.

Another exemplary medical device deployment assembly of the present disclosure is shown at 80 in FIG. 3. The medical device deployment assembly 80 has similarities to the medical device deployment assembly 10 described above and generally includes a retractable sheath 82 and a coaxial inner catheter 84 positioned inside the retractable sheath 82. A medical device 86, such as a stent, is compressed between an outer surface 88 of the coaxial inner catheter 84 and an inner surface 90 of the retractable sheath 82. A spring 92, or other similar member provided a spring force, is positioned inside the retractable sheath 82, and a pusher band 94 is positioned inside the retractable sheath 82 between the medical device 86 and the spring 92. The spring 92 biases the medical device deployment assembly 80 toward a deployment configuration, which is shown in FIG. 5. Pre-deployment configurations of the medical device deployment assembly 80 are depicted in FIGS. 3 and 4.

According to the current exemplary embodiment, the coaxial inner catheter 84 includes a first catheter 96 and a second catheter 98 positioned inside the first catheter 96. As shown, the pusher band 94 is attached to move with the second catheter 98, and the spring 92 is positioned between the pusher band 94 and a distal end 100 of the first catheter 96. According to some embodiments, the distal end 100 of the first catheter 96 may include an additional pusher band 102 for restricting proximal movement of the spring 92 beyond the distal end 100 of the first catheter 96. The first catheter 96 may have a fixed position relative to the retractable sheath 82. Alternatively, the medical device deployment assembly 80 may include a relaxed configuration in which the distal end 100 of the first catheter 96 is a long distance $l_3$ from the pusher band 94, as shown in FIG. 3, and a delivery configuration in which the distal end 100 of the first catheter 96 is a short distance $l_4$ from the pusher band 94, as shown in FIG. 4.

Figure 4:
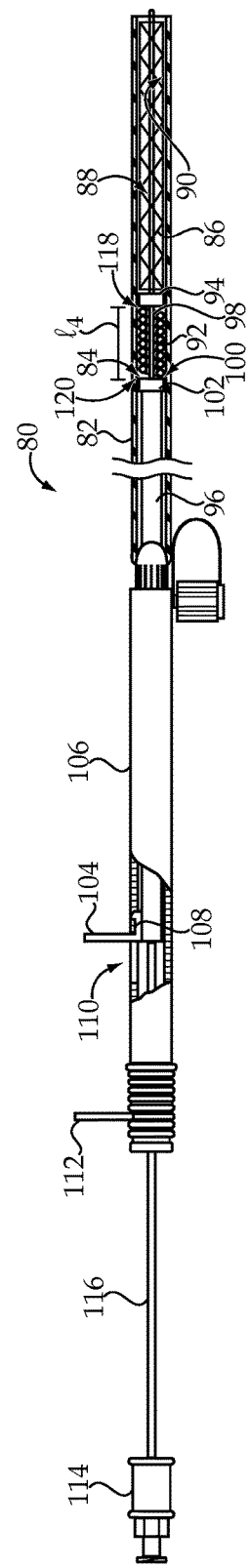
FIG. 4 is a partially sectioned side diagrammatic view of the medical device deployment assembly of FIG. 3, shown in a delivery configuration.
Figure 5:
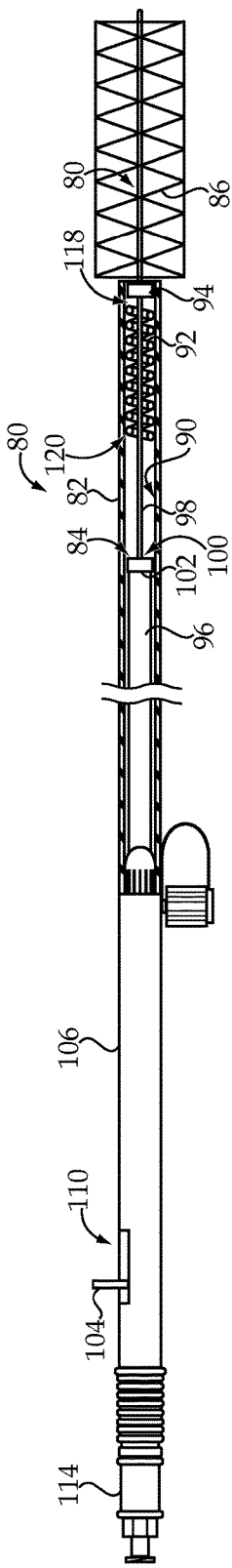
FIG. 5 is a partially sectioned side diagrammatic view of the medical device deployment assembly of FIGS. 3 and 4, shown in a deployment configuration.

A clinician may transition the medical device deployment assembly 80 from the relaxed configuration of FIG. 3 to the delivery configuration of FIG. 4 prior to deployment. According to some embodiments, a catch 104 may be disengaged in the relaxed configuration, but engaged in the delivery configuration to hold the first catheter 96 relative to the second catheter 98 against a pre-load of the spring 92. For example, the catch 104 may be operatively coupled with the first catheter 96 and supported within a handle 106 of the medical device deployment assembly 80. To compress, or load, the spring 92, the catch 104, and thus first catheter 96, may be moved distally and engaged with a complementary structure 108, such as a projection, of the handle 106 that maintains the delivery configuration. The handle 106 may include a slot 110 to permit connection of the catch 104 to the first catheter 96 through the handle 106 and permit axial movement of the catch 104. It should be appreciated that alternative structures and arrangements for transitioning between the relaxed and delivery configurations, and locking the delivery configuration, may be incorporated into the medical device deployment assembly 80.

To move the medical device deployment assembly 80 from the delivery configuration of FIG. 4 to the deployment configuration of FIG. 5, the clinician may remove a locking pin 112 to permit movement of the handle 106 and retractable sheath 82 relative to the coaxial inner catheter 84. Next, the clinician may maintain a stationary position of a hub 114, while proximally retracting the handle 106 over a cannula 116. In addition, the clinician may release the catch 104 such that the force of the spring 92 may be released and used to initiate the deployment. The catch release may occur before, after, or simultaneously with the removal of the locking pin 112. With the catch 104 released, a distal end 118 of the spring 92 may apply a distal force against the pusher band 94, while a proximal end 120 of the spring 92 may apply a proximal force against the distal end 100 of the first catheter 96, or additional pusher band 102. With the retractable sheath 82 proximally retracted, as shown, the medical device 86 may be permitted to deploy, such as by expanding in a radial direction.

INDUSTRIAL APPLICABILITY

The present disclosure is generally applicable to medical device deployment systems. More specifically, the present disclosure is applicable to deployment systems for deploying self-expanding medical devices, such as stents, grafts, filters, and the like. Further, the present disclosure is applicable to spring assisted medical device deployment systems.

Referring generally to FIGS. 1-7, and more particularly to the embodiment of FIGS. 1 and 2, a medical device deployment assembly 10 includes a catheter 18 positioned inside a retractable sheath 34. According to the exemplary embodiment, the retractable sheath 34 may be a stepped sheath 56 with a long proximal segment 58 having a small diameter $d_2$ and a short distal segment 60 having a large diameter $d_1$, which is greater than the small diameter $d_2$. A medical device 30, such as a stent 32, is compressed between an outer surface 46 of the catheter 18 and an inner surface 44 of the retractable sheath 34. A spring 48 is positioned inside the retractable sheath 34, and a pusher band 50 is positioned inside the retractable sheath 34 between the medical device 30 and the spring 48. The spring 48 biases the medical device deployment assembly 10 toward a deployment configuration, depicted in FIG. 2, in which a distal tip 66 of the retractable sheath 34 is proximal to a proximal tip 68 of the medical device 30.

Figure 6:
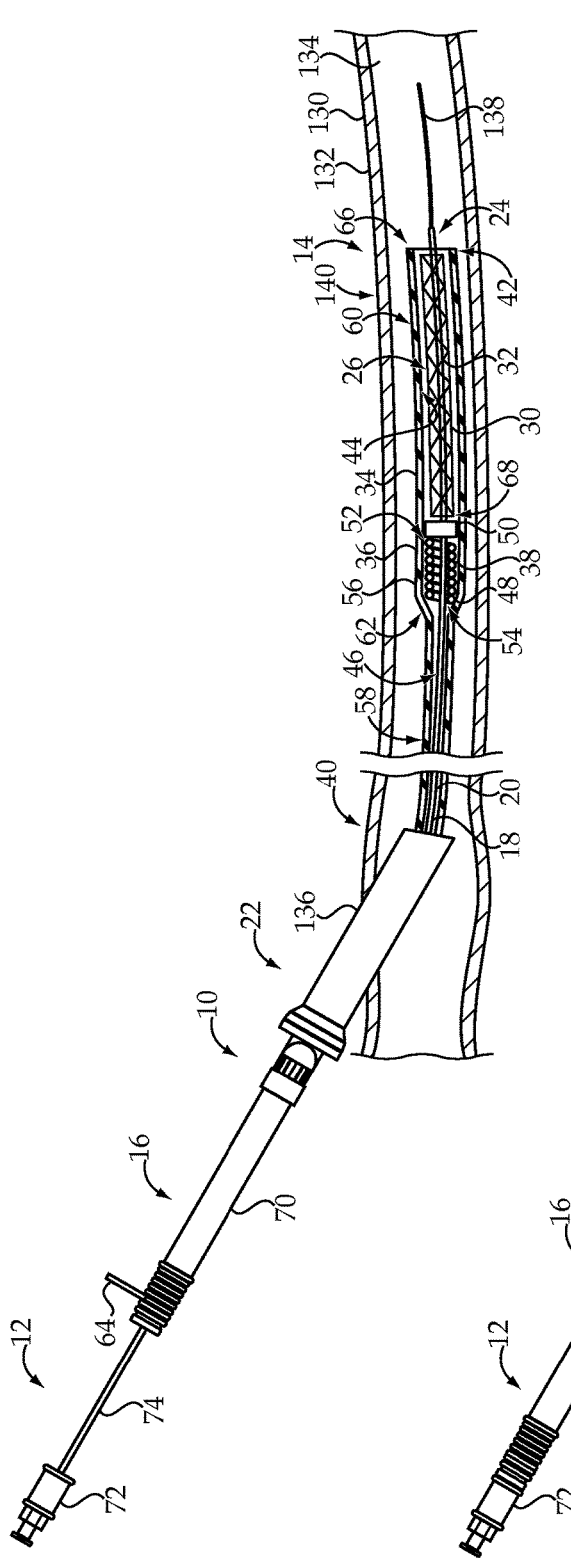
FIG. 6 is a side diagrammatic view of a vascular structure of a patient at one stage of a medical device deployment procedure using the medical device deployment assembly of FIGS. 1 and 2.
Figure 7:
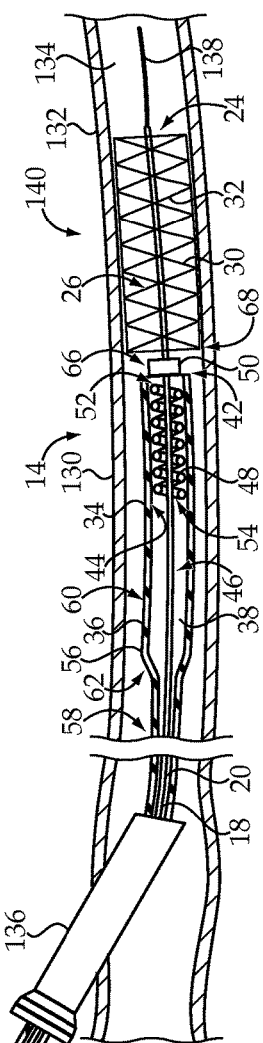
FIG. 7 is a side diagrammatic view of the vascular structure at another stage of the medical device deployment procedure.

Referring now to FIGS. 6 and 7, a percutaneous vascular procedure using the medical device deployment assembly 10 of FIGS. 1 and 2 will be discussed with reference to a vascular structure 130 of a patient. The vascular structure 130, as should be appreciated, may include a vessel wall 132 defining a lumen 134. A clinician may first position a needle, or introducer 136, through the skin of a patient to gain access to the vascular structure 130. At a next stage of the procedure, a clinician may insert a conventional wire guide 138 through a tube of the introducer 136 and into the vascular structure 130.

As shown in FIG. 6, a distal portion 14 of the medical device deployment assembly 10 may be inserted through the introducer 136 and over the wire guide 138. In particular a hollow elongate body 20 of the catheter 18 may be advanced over the wire guide 138. The distal portion 14 of the medical device deployment assembly 10 may be advanced toward a deployment location 140 within the body lumen 134 with the medical device deployment system 10 in a pre-deployment configuration, as described with respect to FIG. 1, in which a hub 72 is located a deployment distance $l_2$, which is greater than a length $l_1$ of the medical device 30, proximal of a handle 70, and the spring 48 is compressed between the pusher band 50 and a transition shoulder 62 of the stepped sheath 56 where the sheath 56 transitions from the long proximal segment 58 to the short distal segment 60. A locking pin 64 may fix the relative positions of the catheter 18 and the retractable sheath 34 in the pre-deployment configuration, and may maintain a compressed state of the spring 48.

As shown in FIG. 6, the medical device 30 of the medical device deployment assembly 10 may be positioned at the deployment location 140. The medical device 30 may then be deployed at the deployment location 140. In particular, the clinician may slide the retractable sheath 34 with respect to the catheter 18 while maintaining the catheter 18 stationary with respect to the deployment location 140. For example, to move the medical device deployment assembly 10 into the deployment configuration, which is shown in FIG. 7 and described above with respect to FIG. 2, the locking pin 64 may be removed and the clinician may maintain a stationary position of the hub 72, while proximally retracting the handle 70 along the cannula 74. The handle 70 is moved toward, and eventually contacts, the hub 72 in the deployment configuration.

The spring 48 may provide an additional force as the medical device deployment assembly 10 begins the transition from the pre-deployment configuration to the deployment configuration. For example, the spring 48 may push the retractable sheath 34 with respect to the catheter 18 with a pushing force. In particular, the proximal end 54 of the spring 48 may provide a proximal force against the transition shoulder 62 of the retractable sheath 34. The sliding force applied by the clinician to the handle 70 is combined with the pushing force provided by the spring 48 to initiate the sliding movement of the retractable sheath 34 with respect to the catheter 18. According to some embodiments the force provided by the spring 48 may be greater than five Newtons.

With the retractable sheath 34 proximally retracted, as shown, the medical device 30 may be permitted to deploy, such as by expanding in a radial direction. It should be appreciated that the retractable sheath 34 is slid a deployment distance $l_2$ that is greater than a length $l_1$ of the medical device 30 to properly deploy the medical device 30. According to the alternative embodiment of FIGS. 3-5, a spring 92 may be compressed between a pusher band 94 and a distal end 100 of a first catheter 96. As described above, the clinician may transition the medical device deployment assembly 80 from the relaxed configuration of FIG. 3 to the delivery configuration of FIG. 4 prior to deployment. For example, a catch 104 may be operatively coupled with the first catheter 96 and supported within a handle 106 of the medical device deployment assembly 80. To compress, or load, the spring 92, the catch 104, and thus first catheter 96, may be moved distally and engaged with a complementary structure 108, such as a projection, of the handle 106 that maintains the delivery configuration.

Alternative embodiments for compressing a spring member prior to deployment are also contemplated. Further, it is contemplated that alternative components may be utilized to transfer a proximal and/or distal force from the spring member. According to one example, the spring member may be made from a shape memory material, such as nitinol, and may be in a compressed state at room temperature and an extended state when surrounded by a higher temperature, such as when positioned in the body. Thus, advancing the deployment device, including the spring member, into the vascular lumen where the stent, or other medical device is to be deployed, may "activate" the spring member and initiate or assist with deployment.

The medical device deployment system described herein provides an effective means for deploying medical devices of various sizes and configurations. The spring force provided within the medical device deployment system may be particularly useful when deploying relatively large medical devices and/or medical devices including specialized coatings, which may require a relatively high deployment force. The spring force provided may be sufficient to initiate and/or assist in the retraction of the sheath and deployment of the medical device.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A medical device deployment assembly, comprising:
   a handle having a proximal end;
   a retractable sheath with a distal tip, and a proximal end attached to move with the handle;
   a catheter positioned inside the retractable sheath and having a proximal end;
   a medical device compressed between an outer surface of the catheter and an inner surface of the retractable sheath, and having a proximal tip;
   a spring positioned inside the retractable sheath;
   a pusher band attached to move with the catheter relative to the sheath, disposed at a fixed position on the catheter, and positioned inside the retractable sheath between the medical device and the spring;
   wherein the spring biases the medical device deployment assembly toward a deployment configuration in which the distal tip of the retractable sheath is proximal to the proximal tip of the medical device; and
   wherein the proximal end of the handle is closer to the proximal end of the catheter than to the spring.

2. The medical device deployment assembly of claim 1, further including:
   a hub and cannula operatively coupled to the proximal end of the catheter;
   wherein the hub is located a deployment distance proximal of the handle in a pre-deployment configuration, the deployment distance is greater than a length of the medical device, and the hub contacts the handle in the deployment configuration.

3. The medical device deployment assembly of claim 1, wherein the spring is compressed with a pre-load of at least five Newtons.

4. The medical device deployment assembly of claim 1, wherein the retractable sheath is a stepped sheath with a long proximal segment having a small diameter and a short distal segment having a large diameter, and the spring is compressed between the pusher band and a transition shoulder of the stepped sheath where the stepped sheath transitions from the long proximal segment to the short distal segment.

5. The medical device deployment assembly of claim 1, wherein the catheter is a second catheter and the medical device deployment assembly further includes a first catheter, and the second catheter is positioned inside the first catheter, and wherein the pusher band is attached to move with the second catheter and the spring is compressed between the pusher band and a distal end of the first catheter.

6. The medical device deployment assembly of claim 5, wherein the medical device deployment assembly further includes a relaxed configuration in which the distal end of the first catheter is a long distance from the pusher band, and a delivery configuration in which the distal end of the first catheter is a short distance from the pusher band.

7. The medical device deployment assembly of claim 6, further including a catch that is disengaged in the relaxed configuration, but engaged in the delivery configuration to hold the first catheter relative to the second catheter against a pre-load of the spring.

8. The medical device deployment assembly of claim 1, wherein a ratio of a length of the medical device to an outer diameter of the retractable sheath is greater than fifty.

9. The medical device deployment assembly of claim 8, further including:
 a hub and cannula operatively coupled to the proximal end of the catheter;
 wherein the hub is located a deployment distance proximal of the handle in a pre-deployment configuration, the deployment distance is greater than a length of the medical device, and the hub contacts the handle in the deployment configuration.

10. The medical device deployment assembly of claim 9, wherein the spring is compressed with a pre-load of at least five Newtons.

11. A method of operating a medical device deployment assembly that includes a catheter positioned inside a retractable sheath, and the retractable sheath is attached to move with a handle; the catheter includes a proximal end, and the handle includes a proximal end; a medical device compressed between an outer surface of the catheter and an inner surface of the retractable sheath; a spring positioned inside the retractable sheath; and a pusher band attached to move with the catheter relative to the sheath, disposed at a fixed position on the catheter, and positioned inside the retractable sheath between the medical device and the spring, the method comprising the steps of:
 positioning the medical device of the medical device deployment assembly at a deployment location; and
 deploying the medical device at the deployment location;
 wherein the deploying step includes moving the handle, which has the proximal end that is closer to the proximal end of the catheter than to the spring, to slide the retractable sheath with respect to the catheter while maintaining the catheter stationary with respect to the deployment location;
 wherein the sliding step includes pushing the retractable sheath with respect to the catheter with a pushing force using the spring.

12. The method of claim 11, wherein the step further includes applying a sliding force to the handle attached to a proximal end of the retractable sheath, wherein the sliding force and the pushing force of the spring combine to initiate sliding movement of the retractable sheath with respect to the catheter.

13. The method of claim 12, wherein the retractable sheath is slid a deployment distance that is greater than a length of the medical device during the deploying step.

14. The method of claim 13, wherein the pushing step includes applying a force greater than five Newtons with the spring.

15. The method of claim 14, further including a step of compressing the spring between the pusher band and a transition shoulder of the retractable sheath where the retractable sheath transitions from a long proximal segment to a short distal segment.

16. The method of claim 12, wherein the catheter is a second catheter, the medical device deployment assembly further includes a first catheter, and the second catheter is positioned inside the first catheter, and the pusher band is attached to move with the second catheter, and wherein the method further includes compressing the spring between the pusher band and a distal end of the first catheter.

17. The method of claim 16, further including:
 moving the medical device deployment assembly from a relaxed configuration to a deployment configuration prior to the deploying step;
 wherein the distal end of the first catheter is a long distance from the pusher band in the relaxed configuration, and the distal end of the first catheter is a short distance from the pusher band in the delivery configuration;
 wherein the moving step includes applying a pre-load to the spring.

18. The method of claim 17, further including engaging a catch at an end of the medical device deployment assembly moving step, wherein the catch is disengaged in the relaxed configuration, but engaged in the delivery configuration to hold the first catheter relative to the second catheter against the pre-load of the spring.

19. The method of claim 11, wherein a ratio of a length of the medical device to an outer diameter of the retractable sheath is greater than fifty.

20. The method of claim 11, further including sliding the medical device deployment assembly over a wire guide during the positioning step.

* * * * *